(12) United States Patent
Devin-Baudoin et al.

(10) Patent No.: US 6,953,484 B2
(45) Date of Patent: Oct. 11, 2005

(54) USE OF PARTICULAR AMINOSILICONES AS A PRE- OR POST-TREATMENT OF PROCESSES FOR BLEACHING KERATIN FIBERS

(75) Inventors: Priscille Devin-Baudoin, Vanves (FR); Anne Sabbagh, Rueil Malmaison (FR)

(73) Assignee: L'Oreal, S.A., Paris (FR)

( * ) Notice: Subject to any disclaimer, the term of this patent is extended or adjusted under 35 U.S.C. 154(b) by 56 days.

(21) Appl. No.: 10/290,150

(22) Filed: Nov. 8, 2002

(65) Prior Publication Data

US 2003/0121108 A1 Jul. 3, 2003

(30) Foreign Application Priority Data

Nov. 8, 2001 (FR) .......................................... 01 14471

(51) Int. Cl.⁷ .............................. D06L 3/04; D06L 3/00; A61K 7/13
(52) U.S. Cl. ................................. 8/101; 8/111; 424/62; 424/70.1; 424/70.2; 424/70.11; 424/70.19; 424/70.27; 424/70.31; 132/202; 132/208
(58) Field of Search ............................. 8/101, 111, 581; 424/62, 70.1, 70.2, 70.11, 70.19, 70.27, 70.31; 132/202, 208

(56) References Cited

U.S. PATENT DOCUMENTS

| 5,925,341 A | * | 7/1999 | Cervantes et al. | ........ 424/78.03 |
| 2002/0006389 A1 | | 1/2002 | Restle et al. | ................ 424/70.1 |

FOREIGN PATENT DOCUMENTS

| EP | 0 890 355 | 1/1999 |
| EP | 0 974 335 | 1/2000 |
| GB | 2 151 454 | 12/1984 |

\* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

A pre- or post-treatment composition for the process for bleaching human keratin fibers, such as hair, comprising at least one particular aminosilicone as well as processes for bleaching human keratin fibers, such as hair, comprising a pre- or post-treatment with a composition comprising at least one particular aminosilicone.

39 Claims, No Drawings

USE OF PARTICULAR AMINOSILICONES AS A PRE- OR POST-TREATMENT OF PROCESSES FOR BLEACHING KERATIN FIBERS

This disclosure relates to the use, as a pre- or post-treatment of a process for bleaching human keratin fibers, such as hair, of a composition comprising at least one particular aminosilicone, as defined herein.

This disclosure also relates to processes for bleaching human keratin fibers, such as hair, comprising a pre-or post-treatment with a composition comprising at least one particular aminosilicone.

The natural shades of dark hair may be lightened in a long-lasting manner by means of bleaching treatments. This is likewise the case for shades artificially given to the hair by means of direct dyes or oxidation dyes, and which it is desired to remove.

The bleaching compositions used in these treatments comprise ready-to-use thickened aqueous hydrogen peroxide compositions. For example, these treatments may be in the form of anhydrous products (powders or creams) comprising alkaline compounds (amines and alkaline silicates), and a peroxygenated oxidizing reagent such as ammonium or alkali metal persulfates, perborates or percarbonates, which are diluted at the time of use with an aqueous hydrogen peroxide composition.

However, these highly efficient treatments may cause sensitization of the hair; the hair becomes drier and more difficult to disentangle, with a coarse feel.

Other bleaching treatments use ready-to-use compositions comprising anhydrous products (powders or creams) comprising reducing agents, which are mixed at the time of use with an aqueous composition optionally comprising a pH agent. These reducing treatments can also cause sensitization of the hair.

Hitherto, to improve the condition of hair fibers after a bleaching treatment, use has been made of rinse-out or leave-in care products, such as conditioners, treating masks, treating creams or sera.

These care products have the drawback of being temporary and must be renewed each time the hair is washed.

In addition, they usually make the hair lank, rendering it lifeless, with an unnatural slippery coated feel.

There is thus a need to improve the condition of the hair after a bleaching treatment.

After extensive studies in this matter, the inventors have discovered, entirely surprisingly and unexpectedly, that the use, as a pre- or post-treatment on human keratin fibers, such as hair, of a composition comprising at least one particular aminosilicone, allows at least one of these problems to be solved. This discovery forms at least a portion of the basis for at least one embodiment disclosed herein.

A new embodiment therefore relates to the use, as a pre- or post-treatment of a process for bleaching human keratin fibers, such as hair, of a composition comprising at least one aminosilicone comprising at least one aminoethylimino $(C_4-C_8)$alkyl group.

An embodiment of the process is to improve the condition of the hair after bleaching, so that the hair may become at least one of softer, smooth from the root to the end, individualized, light, supple and silky. Moreover, the hair may feel much more natural than when a conditioner of the prior art is used after a bleaching operation. In addition, the hair may disentangle well and may style much more easily. The treatment may have the further advantage of not modifying the lightening power of the bleaching treatment, and the cosmetic effects thus produced may be long-lasting and visible for at least six weeks.

As used herein, the phrase "improvement in the condition of the fiber" means a reduction in the porosity or the alkaline solubility of the fiber and an improvement in at least one cosmetic property, for example, in the smoothness, softness and ease of disentangling and of styling.

This effect can be remanent, i.e., long-lasting.

The porosity is measured by fixing at 37° C. and at pH 10, for two minutes, 2-nitro-para-phenylenediamine at 0.25% in an ethanol/pH 10 buffer mixture (10/90 volume ratio).

The alkaline solubility corresponds to the loss of mass of a sample of 100 mg of keratin fibers under the action of decinormal sodium hydroxide for 30 minutes at 65° C.

Another new embodiment relates to a bleaching process that comprises applying to human keratin fibers, such as hair, which may be wet or dry, washed or unwashed, a composition comprising at least one aminosilicone comprising at least one aminoethylimino$(C_4-C_8)$alkyl group, leaving it to act at room temperature or with a supply of heat, optionally rinsing said fibers and then applying the bleaching composition, washing said fibers, rinsing them and then drying them.

Another new embodiment relates to a bleaching process that comprises applying a bleaching composition to human keratin fibers, such as hair, washing said fibers with shampoo, rinsing them with water and then applying a composition comprising at least one aminosilicone comprising at least one aminoethylimino$(C_4-C_8)$alkyl group to the wet or dry fibers, leaving it to act at room temperature or with a supply of heat, optionally rinsing said fibers and then drying them. According to this post-treatment process, the composition may be applied immediately after bleaching, or after an interval, and repeatedly.

Aminosilicones

The at least one aminosilicone comprising at least one aminoethylimino$(C_4-C_8)$alkyl group has, for example, the following formula:

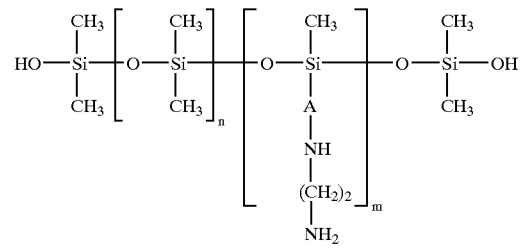

wherein:

A is chosen from linear and branched $C_4-C_8$ alkylene radicals, for example, $C_4$ alkylene radicals, and m and n are numbers such that the sum (n+m) can range, for example, from 1 to 2000 and further, for example, from 50 to 150, n may be a number ranging from 0 to 1999, for example, from 49 to 149, and m may be a number ranging from 1 to 2000, for example, from 1 to 10.

The term "alkylene radical" means divalent saturated hydrocarbon-based groups.

The viscosity of the at least one aminosilicone, for example, can be greater than 25 000 mm²/s at 25° C.

For example, this viscosity can range from 30 000 to 200 000 mm²/s at 25° C. and further, for example, from 30 000 to 150 000 mm²/s at 25° C.

The viscosity of the at least one aminosilicone is measured at 25° C. according to the standard "ASTM 445 Appendix C".

The at least one aminosilicone has a weight-average molecular mass, for example, ranging from 2000 to 1 000 000 and further, for example, from 3500 to 200 000.

The weight-average molecular masses of the at least one aminosilicone is measured by Gel Permeation Chromatography (GPC) at room temperature, as polystyrene equivalents. The columns used are styragel p columns. The eluent is THF, and the flow rate is 1 ml/minute. 200 µl of a solution at 0.5% by weight of silicone in THF are injected. The detection is performed by refractometry and UV-metry.

One new embodiment involves using the at least one aminosilicone in the form of an oil-in-water emulsion. The oil-in-water emulsion may comprise at least one surfactant. The at least one surfactant may be of any nature, for example, cationic and/or nonionic.

The silicone particles in the emulsion may have a mean size ranging, for example, from 3 to 500 nanometers, and further, for example, from 5 to 300 nanometers, even further, for example, from 10 to 275 nanometers and even further, for example, from 150 to 275 nanometers. Such particle size is measured by a laser granulometer.

An example of a silicone corresponding to this formulation is DC2-8299® from the company Dow Corning.

The at least one aminosilicone may be used in the pre- or post-treatment composition in an amount ranging from 0.01% to 20% by weight relative to the total weight of the composition. For example, this amount may range from 0.1% to 15% by weight and further, for example, from 0.5% to 10% by weight relative to the total weight of the composition.

The pre- or post-treatment composition may comprise any ingredient conventionally used in cosmetics, such as in the field of haircare. For example, it may comprise at least one additional surfactant and/or polymer. These surfactants and polymers may be chosen from nonionic, cationic, anionic and amphoteric surfactants and polymers. Among the additional polymers, aminosilicones other than the at least one aminosilicone disclosed herein may be used.

The pre- or post-treatment composition may have a pH ranging from 2 to 11, for example, from 4 to 9.

The pre-or post-treatment composition may be in various forms, such as lotions, gels, creams, shampoos, sticks, mousses or sprays. For some of these forms, it may be packaged in a pump-dispenser bottle or in an aerosol container. In the case of an aerosol, the composition may be combined with a propellant that may be, for example, an alkane or a mixture of alkane, dimethyl ether, nitrogen, nitrous oxide, carbon dioxide and haloalkanes, and also mixtures thereof.

In one new embodiment, the pre- or post-treatment composition may be in the form of a shampoo.

In this case, the composition comprises at least one surfactant, for example, an anionic surfactant. The composition may also comprise a mixture of surfactants comprising at least one anionic surfactant, and at least one other surfactant chosen from nonionic and amphoteric surfactants.

As mentioned above, the post-treatment composition may be applied immediately after bleaching, or after an interval. The expression "after an interval" means an application performed a few hours, one day or several days, for example, from 1 to 60 days, after bleaching.

According to one new embodiment, several applications can be carried out between two bleaching operations.

The number of applications between two bleaching operations may, for example, range from 1 to 60 and further, for example, from 2 to 30.

The bleaching compositions may be reducing or oxidizing.

When said bleaching compositions are reducing, they may be, for example, in the form of ready-to-use compositions comprising anhydrous products (powders or creams) comprising at least one reducing agent, which is mixed, at the time of use, with an aqueous composition optionally comprising a pH agent. The bleaching compositions may also be in the form of aqueous ready-to-use compositions comprising at least one reducing agent at the appropriate pH. The at least one reducing agent may be chosen from, for example, thiols such as cysteine, thiolglycolic acid, thiolactic acid, salts thereof and esters thereof, cysteamine and its salts, ascorbic acid, its salts and its esters, erythorbic acid, its salts and its esters, and sulfites and sulfinates, for example, sodium hydroxymethanesulfinate.

When said bleaching compositions are oxidizing, they comprise at least one oxidizing agent, for example, hydrogen peroxide and compounds capable of producing hydrogen peroxide by hydrolysis, such as urea peroxide or persalts, such as perborates, percarbonates and persulfates.

The oxidizing bleaching compositions may be, for example, in the form of anhydrous products (powders or creams) comprising alkaline compounds (amines and alkaline silicates), and a peroxygenated reagent such as ammonium or alkali metal persulfates, perborates or percarbonates, which may be diluted, at the time of use, with an aqueous hydrogen peroxide composition.

The bleaching compositions may also result from the mixing, at the time of use, of the anhydrous powder of the peroxygenated reagent with an aqueous composition comprising alkaline compounds and another aqueous composition comprising hydrogen peroxide.

The oxidizing bleaching composition may also be in the form of ready-to-use thickened aqueous hydrogen peroxide compositions.

The pre- or post-treatment composition may be used in rinse-out or leave-in mode, i.e., its application may or may not be followed by a rinsing operation.

In the first case, the acting time of the pre- or post-treatment composition ranges from a few seconds to 60 minutes, for example, ranging from 30 seconds to 15 minutes.

The application temperature of the pre- or post-treatment composition may range from 10° C. to 70° C. For example, the application temperature may range from 20 to 60° C., such as room temperature.

The examples that follow are intended to illustrate embodiments disclosed herein, without, however, being limiting in nature.

EXAMPLES

The following composition was prepared:
(expressed as grams of active material)

| Composition | |
|---|---|
| Polydimethylsiloxane sold under the name DC2-8299 ® by Dow Corning | 2 |
| Demineralized water . . . qs | 100 |

The composition was applied to natural chestnut-brown hair:
1/ as a pre-treatment to an oxidizing bleaching using the commercial product Platifiz® from the company L'Oréal;
2/ as a post-treatment to an oxidizing bleaching using the commercial product Platifiz® from the company L'Oréal.

In pre-treatment, the hair was thus treated with this composition for 30 minutes at a temperature of 37° C., rinsed with water, bleached with Platifiz® and rinsed again thoroughly before being dried.

As a post-treatment, the hair was bleached with Platifiz® and rinsed with water, before being treated with the composition, and then rinsed again thoroughly before being dried.

After these treatments, the hair was smoother, softer and easier to disentangle than in the absence of a pre- or post-treatment.

In addition, the level of bleaching was not altered by the treatments.

What is claimed is:

1. A process for bleaching human keratin fibers comprising applying a bleaching composition to said fibers and, either before or after applying said bleaching composition, applying a pre- or post-treatment composition comprising at least one aminosilicone of the following formula:

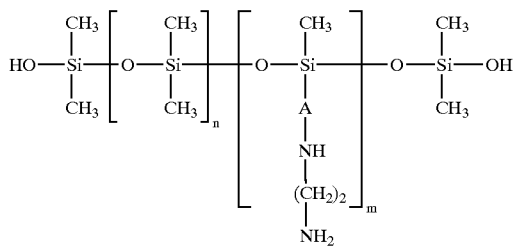

wherein

A is chosen from linear and branched $C_4$–$C_8$ alkylene radicals; m and n are numbers such that the sum (n+m) ranges from 1 to 2000; n is a number ranging from 0 to 1999; and m is a number ranging from 1 to 2000.

2. The process according to claim 1, wherein said human keratin fibers are hair.

3. The process according to claim 1, wherein the sum (n+m) ranges from 50 to 150.

4. The process according to claim 1, wherein n is a number ranging from 49 to 149.

5. The process according to claim 1, wherein m is a number ranging from 1 to 10.

6. The process according to claim 1, wherein A is chosen from linear and branched $C_4$ alkylene radicals.

7. The process according to claim 1, wherein the viscosity of the at least one aminosilicone is greater than 25 000 $mm^2/s$ at 25° C.

8. The process according to claim 1, wherein the viscosity of the least one aminosilicone ranges from 30 000 to 200 000 $mm^2/s$ at 25° C.

9. The process according to claim 8, wherein the viscosity of the least one aminosilicone ranges from 30 000 to 150 0000 $mm^2/s$ at 25° C.

10. The process according to claim 1, wherein the at least one aminosilicone has a weight-average molecular mass ranging from 2000 to 1 000 000.

11. The process according to claim 10, wherein the at least one aminosilicone has a weight-average molecular mass ranging from 3500 to 200 000.

12. The process according to claim 1, wherein the at least one aminosilicone is in the form of an oil-in-water emulsion comprising at least one surfactant.

13. The process according to claim 12, wherein the oil-in-water emulsion comprises at least one surfactant chosen from cationic and nonionic surfactants.

14. The process according to claim 12, wherein the particle size of said at least one aminosilicone ranges from 3 to 500 nanometers.

15. The process according to claim 14, wherein the particle size of said at least one aminosilicone ranges from 5 to 300 nanometers.

16. The process according to claim 15, wherein the particle size of said at least one aminosilicone ranges from 10 to 275 nanometers.

17. The process according to claim 16, wherein the particle size of said at least one aminosilicone ranges from 150 to 275 nanometers.

18. The process according to claim 1, wherein the at least one aminosilicone is present in an amount ranging from 0.01% to 20% by weight relative to the total weight of the composition.

19. The process according to claim 18, wherein the at least one aminosilicone is present in an amount ranging from 0.1% to 15% by weight relative to the total weight of the composition.

20. The process according to claim 19, wherein the at least one aminosilicone is present in an amount ranging from 0.5% to 10% by weight relative to the total weight of the composition.

21. The process according to claim 1, wherein the pre- or post-treatment composition is provided in a form chosen from lotions, gels, creams, shampoos, sticks, mousses and sprays.

22. The process according to claim 1, wherein the pre- or post-treatment composition is packaged in a pump-dispenser bottle or in an aerosol container.

23. The process according to claim 1, wherein the pre- or post-treatment composition is combined with at least one propellant chosen from alkanes, dimethyl ether, nitrogen, nitrous oxide, carbon dioxide and haloalkanes.

24. The process according to claim 1, wherein the pre- or post-treatment composition comprises at least one surfactant chosen from nonionic, cationic, anionic and amphoteric surfactants.

25. The process according to claim 24, wherein the pre- or post-treatment composition comprises a mixture of surfactants comprising at least one anionic surfactant and at least one other surfactant chosen from nonionic and amphoteric surfactants.

26. The process according to claim 1, wherein the pre- or post-treatment composition comprises at least one additional polymer other than the at least one aminosilicone of the following formula:

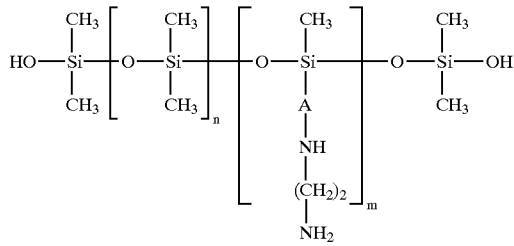

wherein:

A is chosen from linear and branched $C_4$–$C_8$ alkylene radicals; m and n are numbers such that the sum (n+m) ranges from 1 to 2000; n is a number ranging from 0 to 1999; and m is a number ranging from 1 to 2000.

27. The process according to claim 26, wherein said at least one additional polymer is chosen from nonionic, cationic, anionic and amphoteric polymers.

28. The process according to claim 27, wherein said at least one additional polymer is an aminosilicone different than the at least one aminosilicone of the following formula:

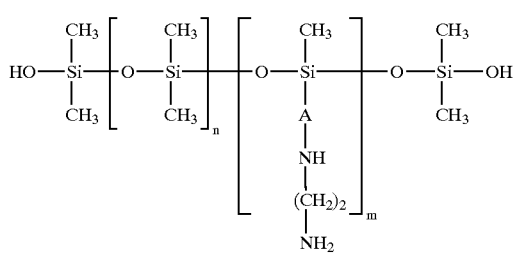

wherein:

A is chosen from linear and branched $C_4$–$C_8$ alkylene radicals; m and n are numbers such that the sum (n+m) ranges from 1 to 2000; n is a number ranging from 0 to 1999; and m is a number ranging from 1 to 2000.

29. The process according to claim 1, wherein the pH of the pre- or post-treatment composition ranges from 2 to 11.

30. The process according to claim 29, wherein the pH of the pre- or post-treatment composition ranges from 4 to 9.

31. The process according to claim 1, wherein the pre-treatment composition or post-treatment composition is left to act for a time ranging from a few seconds to 60 minutes.

32. The process according to claim 31, wherein the pre-treatment or post-treatment composition is left to act for a time ranging from 30 seconds to 15 minutes.

33. The process according to claim 1, wherein said post-treatment composition is applied between two bleaching operations.

34. The process according to claim 33, wherein said post-treatment composition is applied from 1 to 60 times between two bleaching operations.

35. The process according to claim 34, wherein said post-treatment composition is applied from 2 to 30 times between two bleaching operations.

36. A process for improving the condition of human keratin fibers after bleaching, comprising applying to said fibers before or after bleaching a pre- or post-treatment composition comprising at least one aminosilicone of the following formula:

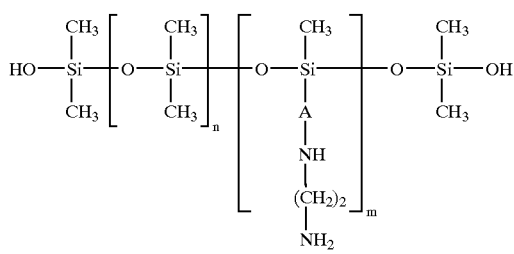

wherein:

A is chosen from linear and branched $C_4$–$C_8$ alkylene radicals; m and n are numbers such that the sum (n+m) ranges from 1 to 2000; n is a number ranging from 0 to 1999; and m is a number ranging from 1 to 2000.

37. A composition for pre-treatment of human keratin fibers prior to bleaching said fibers or for post-treatment of said fibers after bleaching said fibers, said composition comprising at least one aminosilicone of the following formula:

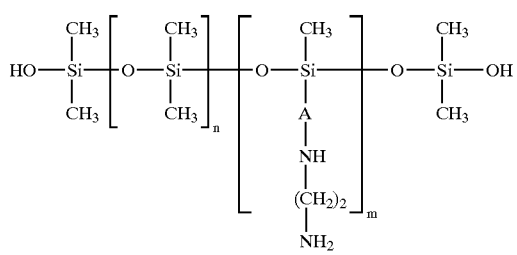

wherein:

A is chosen from linear and branched $C_4$–$C_8$ alkylene radicals; m and n are numbers such that the sum (n+m) ranges from 1 to 2000; n is a number ranging from 0 to 1999; and m is a number ranging from 1 to 2000, wherein said composition is effective for the pre-treatment of human keratin fibers prior to bleaching said fibers or the post-treatment of human keratin fibers after bleaching said fibers.

38. A process for bleaching human keratin fibers comprising applying a bleaching composition to said fibers, leaving said composition on said fibers for a time sufficient to bleach said fibers, and optionally rinsing and optionally drying said fibers, and applying to said fibers, either immediately after said bleaching or after an interval following said bleaching, a post-treatment composition comprising at least one aminosilicone of the following formula:

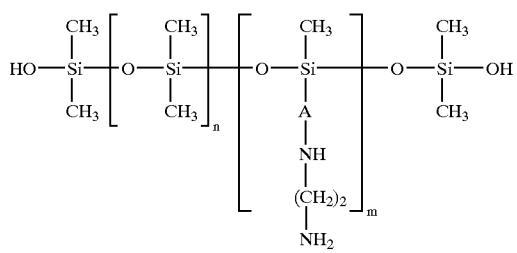

wherein:

A is chosen from linear and branched $C_4$–$C_8$ alkylene radicals; m and n are numbers such that the sum (n+m) ranges from 1 to 2000; n is a number ranging from 0 to 1999; and m is a number ranging from 1 to 2000; and optionally rinsing said fibers and optionally drying said fibers.

39. A process for bleaching human keratin fibers comprising applying to said fibers a pre-treatment composition comprising at least one aminosilicone of the following formula:

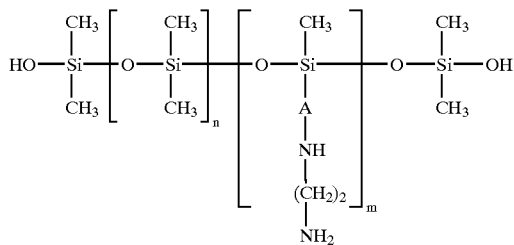

wherein:

A chosen from linear and branched $C_4$–$C_8$ alkylene radicals; m and n are numbers such that the sum (n+m) ranges from 1 to 2000; n is a number ranging from 0 to 1999; and m is a number ranging from 1 to 2000, optionally rinsing said fibers and optionally drying said fibers, applying a bleaching composition to said fibers, leaving said composition on said fibers for a time sufficient to bleach said fibers, and rinsing and drying said fibers.

* * * * *

UNITED STATES PATENT AND TRADEMARK OFFICE
CERTIFICATE OF CORRECTION

PATENT NO. : 6,953,484 B2
DATED : October 11, 2005
INVENTOR(S) : Devin-Baudoin et al.

It is certified that error appears in the above-identified patent and that said Letters Patent is hereby corrected as shown below:

Column 5,
Lines 57-58, "150 0000" should read -- 150 000 --.

Signed and Sealed this

Twenty-seventh Day of December, 2005

JON W. DUDAS
*Director of the United States Patent and Trademark Office*